(12) United States Patent
Yang

(10) Patent No.: US 11,241,536 B2
(45) Date of Patent: Feb. 8, 2022

(54) CLOSED LOOP CONTROL ALGORITHM FOR AN ARTIFICIAL PANCREAS

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 398 days.

(21) Appl. No.: 16/473,248

(22) PCT Filed: Dec. 30, 2016

(86) PCT No.: PCT/CN2016/113693
§ 371 (c)(1),
(2) Date: Jun. 25, 2019

(87) PCT Pub. No.: WO2018/120106
PCT Pub. Date: Jul. 5, 2018

(65) Prior Publication Data
US 2019/0314572 A1    Oct. 17, 2019

(51) Int. Cl.
*A61M 5/172* (2006.01)
*G16H 20/17* (2018.01)
(Continued)

(52) U.S. Cl.
CPC ......... *A61M 5/1723* (2013.01); *A61B 5/4839* (2013.01); *A61M 5/14248* (2013.01); *G16H 20/17* (2018.01); *G16H 50/50* (2018.01); *A61B 5/14532* (2013.01); *A61M 5/14276* (2013.01); *A61M 2005/1726* (2013.01); *A61M 2230/201* (2013.01); *G16H 40/63* (2018.01)

(58) Field of Classification Search
CPC .. A61M 5/14248; A61M 5/1723; G16H 20/17
See application file for complete search history.

(56) References Cited

U.S. PATENT DOCUMENTS

| | | | | |
|---|---|---|---|---|
| 2007/0255122 A1* | 11/2007 | Vol | ..................... | A61B 5/02125 600/301 |
| 2011/0106011 A1* | 5/2011 | Cinar | ..................... | G16H 40/67 604/151 |
| 2014/0005633 A1* | 1/2014 | Finan | ..................... | G16H 20/17 604/504 |

FOREIGN PATENT DOCUMENTS

| | | |
|---|---|---|
| CN | 102576375 | 7/2012 |
| CN | 106137214 | 11/2016 |

OTHER PUBLICATIONS

Muendler, Marc-Andreas. Linear Difference Equations and Autoregressive Processes. Feb. 17, 2000. (Year: 2000).*

(Continued)

*Primary Examiner* — Jenna Zhang
(74) *Attorney, Agent, or Firm* — JCIP Global Inc.

(57) ABSTRACT

The present invention provides a closed loop control method to control an artificial pancreas and the artificial pancreas using this method, comprising constructing an autoregressive model by initiatively introducing the insulin absorption lag factor, calculating an amount of insulin to be delivered at the current time using the autoregressive model and a PID controller respectively, and tuning the parameters of the autoregressive model and the PID controller respectively using the average of the calculation results in order to provide a more accurate prediction of glucose trends and a more desirable amount of insulin delivery.

6 Claims, 3 Drawing Sheets

(51) Int. Cl.
*A61B 5/00* (2006.01)
*A61M 5/142* (2006.01)
*G16H 50/50* (2018.01)
A61B 5/145 (2006.01)
G16H 40/63 (2018.01)

(56) References Cited

OTHER PUBLICATIONS

"International Search Report (Form PCT/ISA/210) of PCT/CN2016/113693," dated Sep. 27, 2017, pp. 1-2.

* cited by examiner

CLOSED LOOP CONTROL ALGORITHM FOR AN ARTIFICIAL PANCREAS

CROSS-REFERENCE TO RELATED APPLICATION

This application is a 371 of international application of PCT application serial no. PCT/CN2016/113693, filed on Dec. 30, 2016. The entirety of the above-mentioned patent application is hereby incorporated by reference herein and made a part of this specification.

FIELD OF THE INVENTION

The present invention relates generally to artificial pancreas and more specifically to a closed loop control algorithm for use with a controller to control insulin delivery to a body.

BACKGROUND TECHNOLOGY

Diabetes is a chronic metabolic disorder caused by an inability of the pancreas to produce sufficient amounts of the hormone insulin, resulting in the decreased ability of the body to metabolize glucose. Recent days, substantial improvements in diabetes therapy have been achieved by the development of insulin delivery devices that relieve the patient of the need for syringes or insulin pens who requires multiple daily injections. The insulin delivery device allows for the delivery of insulin in a manner that bears greater similarity to the naturally occurring physiological processes and can be controlled to follow standard or individually-modified protocols to give the patient better blood glucose control. In addition, insulin delivery devices can be constructed as an implantable device for subcutaneous delivery or as an external device with an infusion set for subcutaneous delivery to the patient via the transcutaneous insertion of a catheter, cannula or a transdermal drug transport.

Blood glucose monitoring is required to achieve acceptable glycemic control. Continuous glucose monitoring (CGM) has been utilized over the last decades with insulin pumps to allow for closed loop control of the insulin being infused into the diabetic patients. To allow for closed-loop control of the infused insulin, proportional-integral-derivative ("PID") controllers have been utilized with mathematical model of the metabolic interactions between glucose and insulin in a person. However, when the PID controllers are applied alone or configured to aggressively regulate the blood glucose levels of a subject, overshooting of the set level can occur due to a lack of dynamic compensation, which is highly undesirable in the context of regulation of blood glucose. In insulin pumps, it is common to use rapid-acting insulin as opposed to the long-acting insulin that is used for injections, because pumps allow changing of insulin profiles, and the rapid-acting insulin is often adopted quickly. However, the effects of the delivery vary by patient and by type of insulin, and current insulin pumps are still limited by the speed of the insulin they are using. Despite important developments in sensor and pump technology, the artificial pancreas must cope with the delays and inaccuracies in both glucose sensing and insulin delivery. This is particularly difficult when a system disturbance, e.g., a meal, occurs and triggers a rapid glucose rise that is substantially faster than the time needed for insulin absorption and action.

SUMMARY OF THE INVENTION

To overcome the deficiencies of the prior art, one purpose of the present invention is to provide a method to control an insulin pump responsive to a controller which receives data from a glucose sensor, comprising the following steps:

receiving a real-time glucose level measurement from the glucose sensor;

calculating an estimated plasma insulin concentration in the body at a predetermined time interval;

constructing an autoregressive model configured to describe the relationship between the estimated plasma insulin and the difference between two successive measurements of the glucose, wherein the lag time from insulin absorption is considered;

computing the initial parameters of the autoregressive model to predict a trend of the glucose change;

calculating an amount of insulin to be delivered at the current time using the autoregressive model and a PID controller respectively, tuning the parameters of the autoregressive model and the PID controller respectively until their calculating results are the same;

determining the amount of insulin to be delivered at the current time according to the calculation results to create a desired future glucose level; and commanding the insulin pump to deliver the determined amount of insulin via the controller.

Alternatively, tuning the parameters of the autoregressive model and the PID controller comprises comparing the calculated amount of insulin to be delivered from the autoregressive model to the calculation result from the PID controller;

if the difference between the calculation results exits, replacing the original calculation results in the autoregressive model and the PID controller with the average of the two calculation results respectively to recalculate the parameters of the autoregressive model and the PID controller;

repeating the above steps until the difference is eliminated.

The steps of the above-identified method are automatically performed via the controller for each of a plurality of the discrete time intervals with updated sensor measurements and can be used as part of the closed loop control algorithm for an artificial pancreas system.

The other purpose of the present invention is to provide an artificial pancreas system using a closed loop control, comprising a glucose sensor configured to continually measure respective glucose levels at discrete time intervals and provide respective glucose measurement data; an insulin pump configured to deliver insulin in response to a delivery control signal; and a controller configured to automatically perform the steps of the above-identified method for each of a plurality of the discrete time intervals.

Alternatively, the controller is one of a processer in the glucose sensor, a processer in the insulin pump, a processer in a handset, or a processing module of a smart device.

The advantages of the present invention can be described in the following ways:

Constructing the autoregressive model by initiatively introducing the insulin absorption lag factor acts as a strong complement to the PID controller in a closed-loop algorithm, for traditional PID controller only responds to a change in the system when it happens. Using both the autoregressive model and the PID controller at the same time makes the calculating results more feasible and reliable in determining insulin delivery amount to create a desirable glucose level in a future time. Furthermore, modifying the parameters of the autoregressive model and the PID controller respectively optimizes the performance of the two algorithms in a paralleled way making them function as each other's dynamic compensation, especially in regard of the typical overshooting of the PID controller. To sum up, the method to control the insulin pump using both the autoregressive model and the PID controller via the controller in the present invention provides more reliable outputs for insulin delivery determination, and can be used as part of the closed loop control algorithm enabling comprehensive and sophisticated functions of a closed loop artificial pancreas.

DETAILED DESCRIPTION

To make the above-mentioned objects, features and advantages of the present invention more obvious and understandable, the embodiments of the present invention are described in the following through specific embodiments.

Figure 1:
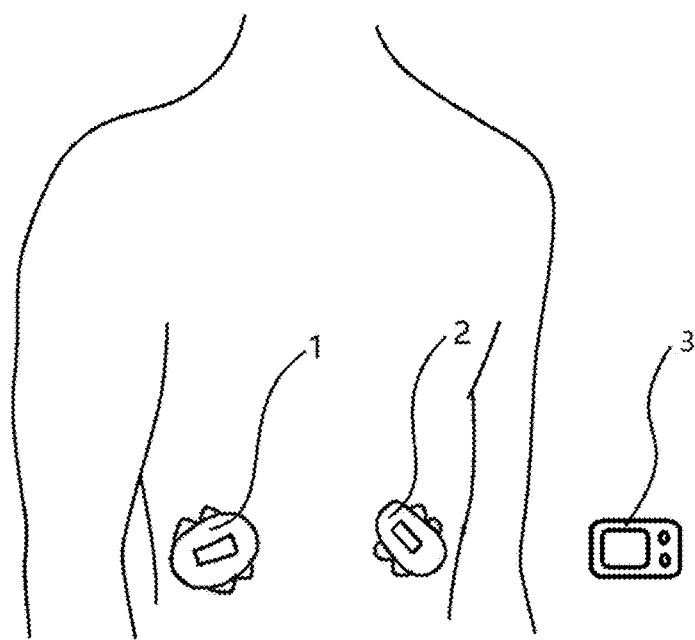
FIG. 1 is a schematic diagram of a patient wearing an artificial pancreas in the present invention.
Figure 2:
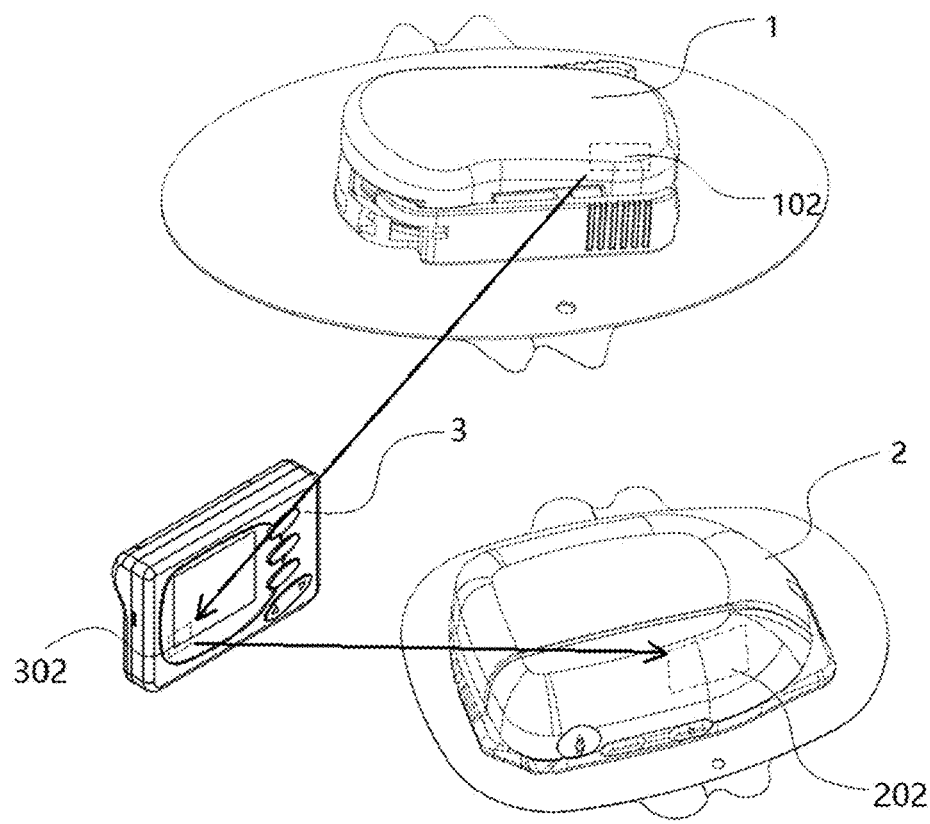
FIG. 2 is a schematic diagram of representative method in the embodiment of the present invention.

Referring to FIG. 1 and FIG. 2, an embodiment of the present invention is provided. FIG. 1 illustrates a patient wearing an artificial pancreas comprising a glucose sensor 1 configured to continually measure respective glucose levels at discrete time intervals and provide respective glucose measurement data, an insulin pump 2 configured to deliver insulin in response to a delivery control signal, and a handset 3 with a processer working as the controller configured to automatically perform the steps of the method in the present invention for each of a plurality of the discrete time intervals.

FIG. 2 illustrates the implementation of the method using the components in FIG. 1. In this embodiment, the glucose sensor 1 measures a current glucose level of the patient and send the glucose information to a controller 302 in the handset 3 via a transmitter 102. The controller automatically performs the steps described in FIG. 4 to determine an insulin delivery amount and generates a corresponding delivery instruction. The delivery instruction is sent to a processor 202 in the insulin pump 2 from the controller 302 to deliver the determined insulin amount, realizing the closed loop control of the artificial pancreas. The steps performed by the controller 302 will be described with FIG. 4 in the following paragraph.

In other embodiments, the controller can be a processer in the glucose sensor, a processer in the insulin pump, or a processing module of a smart device.

Figure 3:
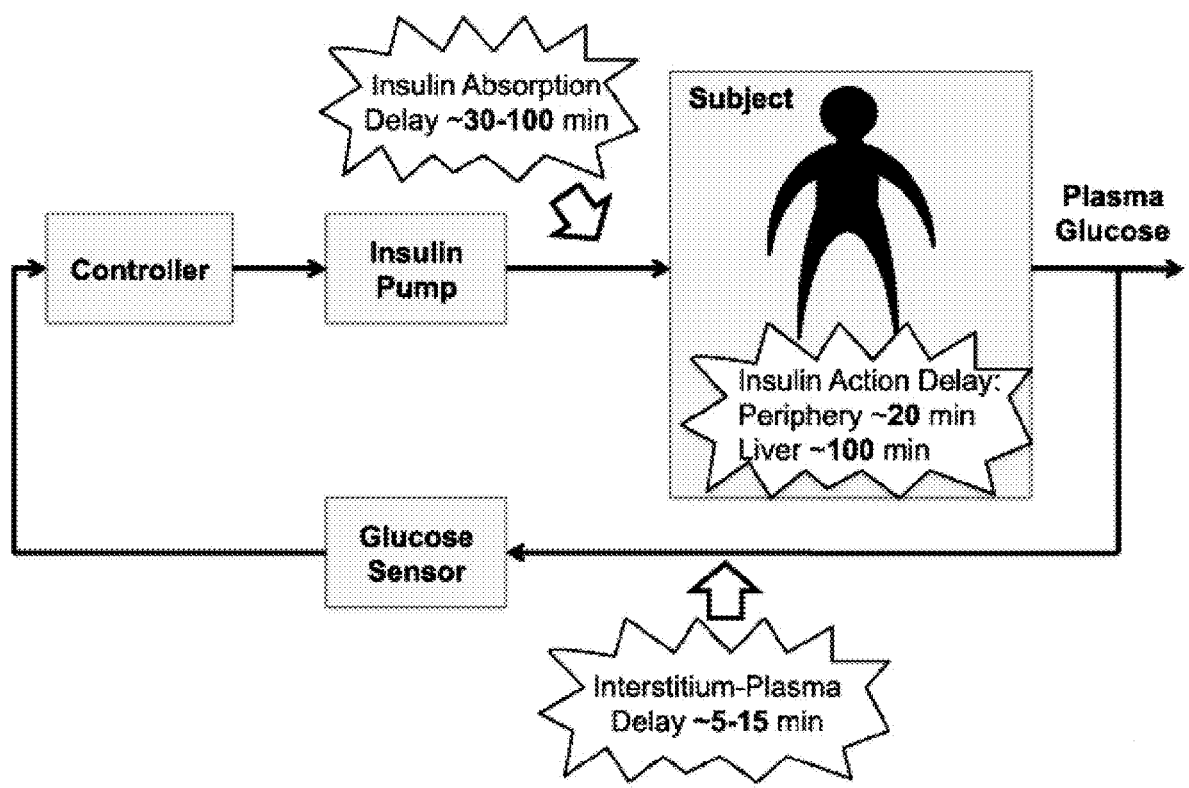
FIG. 3 is a block diagram of three major delay effects in a closed-loop glucose control system.

Referring to FIG. 3, three major delays are indicated in the closed loop control system, insulin absorption delay (30-100 min), insulin action delay on peripheral tissues (20 min) and on the liver (100 min), and sensing delay in the interstitium (5-15 min). Any attempt to speed up the responsiveness of the closed loop may result in unstable system behavior and system oscillation, and any attempt for a preferential closed loop control is to solve the dilemma: to find a trade-off between slow-pace regulation well suited to mild control actions applicable to quasi-steady state (e.g., overnight), and postprandial regulation calling for prompt corrections.

Figure 4:
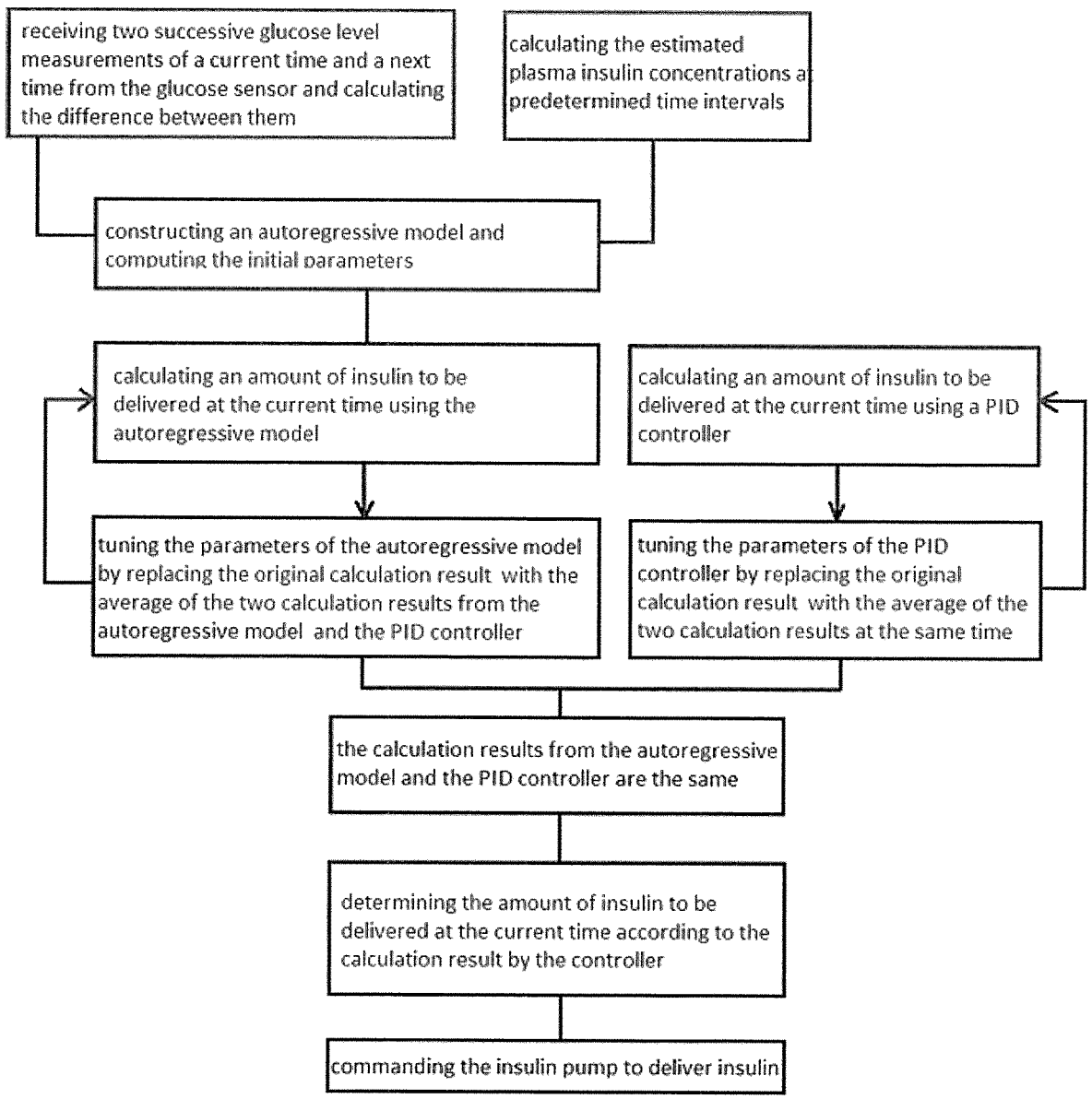
FIG. 4 is a flow chart of representative method in the embodiment of the present invention.

FIG. 4 provides an embodiment of the steps of the method in the present invention in a simplified way. Firstly, receiving two successive glucose level measurements of a current time and a next time from the glucose sensor and calculating the difference between them; calculating the estimated plasma insulin concentrations at predetermined time intervals. Next, constructing an autoregressive model and computing the initial parameters of the autoregressive model with the variables obtained from the previous step. The following steps are performed by the controller at the same time to calculate an amount of insulin to be delivered at the current time using the autoregressive model and a PID controller respectively which generate two calculation results likely different from each other. In the next step, replacing the original calculation results in the autoregressive model and the PID controller with the average of the two calculation results respectively to recalculate the parameters and repeating the previous steps until the difference of the calculation results from the autoregressive model and the PID controller is eliminated, then determining the amount of insulin to be delivered at the current time according to the calculation result by the controller and commanding the insulin pump to start delivery.

The Autoregressive Model

The method of constructing the autoregressive model is to introduce the insulin absorption delay factor into the conventional glucose-insulin relationship initiatively. Considering the lag time from subcutaneous delivery to appearing in the blood stream, the amount of insulin appearing in the blood stream would not be the same as the amount of insulin delivered, and the estimated plasma insulin can be calculated as:

$$Ip(t) = \sum_{i=0}^{t-T_0} \frac{I_B(t_i)}{K_{cl}(\tau_2 - \tau_1)} \int_{t-T_0-T_1}^{t-T_0} (e^{-(t-t_i)/\tau_2} - e^{-(t-t_i)/\tau_1}) dt$$

Where, t represents time;

$T_0$ represents time of insulin absorption delay, 30 minutes in this embodiment;

$T_1$ represents time of insulin delivery cycle, 15 minutes in this embodiment;

$\tau_1$ and $\tau_2$ are time constants (in min) associated with the subcutaneous absorption of insulin;

Kcl represents insulin clearance, and $I_B$ represents the magnitude of the impulse (bolus) of insulin delivered at time t=0;

$I_{p(t)}$ represents the estimated plasma insulin concentration at time $(t-T_0)$;

Next, constructing the autoregressive model which can be described as:

$Y_{t'} = kI_{p(t)} + b$

Where, $I_{p(t)}$ represents the estimated plasma insulin concentration at time $(t-T_0)$;

$Y_{t'}$ represents the difference between two successive glucose measurements;

and k and b are parameters.

In some preferred embodiments, the relationship between the estimated plasma insulin concentration and the difference between two successive measurements of the glucose can be described as the following matrix (the time interval for every update of the sensor measurement is set as 2 minutes in this embodiment):

$$\begin{bmatrix} y(n) \\ y(n-1) \\ \ldots \\ y(n-k) \end{bmatrix} = \begin{bmatrix} C(n-t) & 1 \\ C(n-t-1) & 1 \\ \ldots \\ C(n-t-k) & 1 \end{bmatrix} * \begin{bmatrix} k \\ b \end{bmatrix}$$

Where, $Y_{(n)}$ represents the difference between the glucose measurements at t and t minus 2 min;

$Y_{(n-1)}$ represents the difference between the glucose measurements at t minus 2 min and t minus 4 min;

$Y_{(n-k)}$ represents the difference between the glucose measurements at t minus 2k min and t minus 2(k+1) min;

$C_{(n-t)}$ represents the estimated plasma insulin concentration at t;

$C_{(n-t-1)}$ represents the estimated plasma insulin concentration at t minus 2 min;

$C_{(n-t-k)}$ represents the estimated plasma insulin concentration at t minus 2k min;

So the values of the parameters k and b can be approached by:

$$\begin{bmatrix} k \\ b \end{bmatrix} = inv\left(\begin{bmatrix} C(n-t) & 1 \\ C(n-t-1) & 1 \\ \ldots \\ C(n-t-k) & 1 \end{bmatrix}\begin{bmatrix} C(n-t) & 1 \\ C(n-t-1) & 1 \\ \ldots \\ C(n-t-k) & 1 \end{bmatrix}\right)\begin{bmatrix} C(n-t) & 1 \\ C(n-t-1) & 1 \\ \ldots \\ C(n-t-k) & 1 \end{bmatrix}\begin{bmatrix} y(n) \\ y(n-1) \\ \ldots \\ y(n-k) \end{bmatrix}$$

After obtaining the values of k and b, the desirable future glucose level can be calculated using the autoregressive model. By comparing the estimated future glucose level to the desired glucose level, the insulin amount to be delivered at the current time can be calculated.

In particular embodiments, the difference between the plasma glucose and the insulin concentration is assumed to fit a linear relationship. The following matrix is applied to calculate the parameters $k_1$, $k_2$ and b.

$$\begin{bmatrix} y(n) \\ y(n-1) \\ \ldots \\ y(n-k) \end{bmatrix} = \begin{bmatrix} C^2(n-t) & C(n-t) & 1 \\ C^2(n-t-1) & C(n-t-1) & 1 \\ \ldots & \ldots & \ldots \\ C^2(n-t-k) & C(n-t-k) & 1 \end{bmatrix} * \begin{bmatrix} k_1 \\ k_2 \\ b \end{bmatrix}$$

After obtaining the values of $k_1$, $k_2$ and b, calculating the amount of insulin to be delivered using the autoregressive model. Then the calculation results from the autoregressive model and the PID algorithm are compared and used to modify the parameters of the PID controller.

The PID Controller

While applying the autoregressive model to calculate the amount of insulin to be delivered at the current time $t_0$, the controller is also applying a PID algorithm to calculate the amount of insulin to be delivered at the current time $t_0$ and its simplified model can be described as:

$$u(t) = K_p(Y - Y_{des}) + K_i \int_0^t (Y - Ydes) \cdot dt + K_d \frac{dY}{dt} + I_{bas}$$

And in its discrete form:

$$P(n) = K_p(Y - Y_{des})$$

$$I(n) = I(n-1) + K_i(Y - Y_{des})$$

$$D(n) = K_d \frac{dY}{dt(n)}$$

Where,

P(n) is the proportional component of the insulin delivery amount;

I(n) is the integral component of the insulin delivery amount;

D(n) is the derivative component of the insulin delivery amount;

$K_p$ is a proportional gain coefficient;

$K_i$ is an integral gain coefficient;

$K_d$ is a derivative gain coefficient;

Y represents a present glucose level;

$Y_{des}$ represents a desirable glucose level;

t represents time since last sensor calibration;

$I_{bas}$ represents a standard daily basal insulin of a particular subject.

U(t) represents the command sent to the insulin pump.

In some embodiments, the proportional gain $K_p$ is determined using the following equation from published literature:

$$K_p = I_{req}/135$$

Where, $I_{req}$ represents the daily insulin requirement of a particular subject.

Once $K_p$ is measured, the derivative and integral gains are calculated using ratios. The ratio of $K_d/K_p$ can be set to the dominant time constant for insulin action, ranging from 20-40 minutes and preferably 30 minutes. For instance, calculating $K_d$ given $K_p$ using a time constant of 30 minutes, yields the following relationship:

$$K_d = 30 K_p$$

In a similar fashion, the ratio of $K_d/K_i$ can be set to the average ratio from measurements.

In particular embodiments, the insulin amount calculated using the PID controller can be described as:

$$u(t) = k_p e(t) + \frac{k_p}{T_i} \int_0^t e(t)dt + k_p T_d \frac{de(t)}{dt} - \gamma_1 I_s(t) = \gamma_2 I_p(t) - \gamma_3 I_E(t) + C$$

Where,

γ is a correction factor which is a constant determined from the type of insulin and the infusion site of the body;

$I_s$ is a correction factor of the infusion site;

$I_p$ is a correction factor of the estimated plasma insulin;

$I_E$ is a correction factor of the effect-site compartments;

And $K_p$ is calculated given $K_d$ using the time constant of 30 minutes:

$$K_p = K_d/30$$

And $K_d$ is calculated using the equation:

$$K_d = \frac{W}{Si}Q$$

Where,

W represents the body weight of the particular subject;

Si represents the insulin sensitivity of the particular subject;

Q is a constant obtained from data in published literature.

Modification of Parameters of the AR Model and the PID Controller $I_{p(t)}$, the calculated insulin amount to be delivered at the current time $t_0$ using the autoregressive model, and U(t), the calculated insulin amount using PID algorithm are compared, and if the difference is found to be zero, the insulin pump will receive an instruction to deliver the calculated insulin amount.

If the difference between $I_{p(t)}$ and U(t) is not zero, $I_{p(t)}$ in the autoregressive model and U(t) in the PID algorithm are replaced with the average of $I_{p(t)}$ and U(t) to recalculate the parameters k and b in the autoregressive model and $K_p$, $K_i$, $K_d$ in the PID algorithm at the same time under the condition of fixing the ratio between $K_p$ and $K_d$ as well as $K_i$ and $K_d$. Then the $I_{p(t)}$ and U(t) are calculated again using the autoregressive model with modified parameters k' and b' and the PID algorithm with modified coefficients $K_p'$, $K_i'$, $K_d'$, and the steps of comparing, averaging, and replacing the originals with the averages are repeated to recalculate the parameters in the autoregressive model and the PID algorithm respectively until the difference between $I_{p(t)}$ and U(t) is zero.

When the calculation results of the amount of insulin to be delivered at the current time $t_0$ from the autoregressive model and the PID algorithm are the same, it can be considered that it is the preferential amount of insulin to be delivered at the current time $t_0$ to provide a desirable glucose level at time $t_2$ when the insulin being delivered at the current time $t_0$ will start to appear in the blood stream at time $t_2$, so the controller generates a delivery signal commanding the insulin pump to deliver corresponding amount of insulin.

At each and every time when the glucose measurement is updated by the glucose sensor, all the steps identified above are repeated for a new calculation of the insulin delivery amount of the current time.

In other embodiments, all of the parameters $K_p$, $K_i$ and $K_d$ used in the PID algorithm are estimated. In additional embodiments, one or more parameters are measured, while at least one parameter is estimated from literature.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. A method to control an insulin pump responsive to a controller which receives data from a glucose sensor, the method comprising performing the following steps automatically via the controller:

receiving a plurality of glucose level measurements from the glucose sensor;

calculating an estimated plasma insulin concentration in a blood stream in a body at a predetermined time interval based on an amount of an insulin delivered by the insulin pump, and a lag time from a time of the insulin being delivered to a time of the insulin entering the blood stream;

constructing an autoregressive model configured to describe a relationship between the estimated plasma insulin concentration at a time t and a difference between two successive glucose level measurements at the times t and t-k, wherein k is equal to the predetermined time interval;

computing a plurality of parameters of the autoregressive model by using a plurality of sets of the estimated plasma insulin concentration and the glucose level measurements at a plurality of times;

calculating an amount of insulin to be delivered at a current time using the autoregressive model and a proportional-integral-derivative (PID) controller respectively, wherein the PID controller calculates the amount of insulin to be delivered based on a difference between the glucose level measurement of the current time and a desirable glucose level and a plurality of predetermined gains;

tuning the plurality of parameters of the autoregressive model and the plurality of predetermined gains of the PID controller respectively until calculation results of the amount of insulin to be delivered calculated by using the autoregressive model and the amount of insulin to be delivered calculated by using the PID controller are the same, wherein if the calculation results are not the same, the calculation results of the autoregressive model and the PID controller are replaced by average of the calculation results, respectively, to recompute the plurality of parameters of the autoregressive model and the plurality of predetermined gains of the PID controller; and determining the amount of insulin to be delivered at the current time according to final calculation results from the step of tuning to create a desired future glucose level.

2. The method according to claim 1, wherein the plurality of times comprises a time A and a time B; the autoregressive model comprises relating a blood glucose level of the time B to a plasma insulin of the time A, wherein the insulin delivered at the time A enters the blood stream from the time B.

3. The method according to claim 1, wherein tuning the plurality of parameters of the autoregressive model and the plurality of predetermined gains of the MD controller comprises:

comparing the amount of insulin to be delivered calculated by using the autoregressive model to the amount of insulin to be delivered calculated by using the PID controller; and repeating the steps of tuning and comparing until the difference is eliminated.

4. The method according to claim 1, wherein automatically performing the steps in claim 1 for each of a plurality of discrete time intervals with updated sensor measurements via the controller.

5. An artificial pancreas using a closed loop control, comprising:
   a) a glucose sensor configured to continually measure respective glucose levels at discrete time intervals and provide respective glucose measurement data;
   b) an insulin pump configured to deliver insulin in response to a delivery control signal; and
   c) a controller configured to, for each of a plurality of the discrete time intervals:
   i) receiving a plurality of glucose level measurements from the glucose sensor;
   ii) calculating an estimated plasma insulin concentration in a blood stream in a body at a predetermined time interval based on an amount of an insulin delivered by the insulin pump, and a lag time from a time of the insulin being delivered to a time of the insulin entering the blood stream;
   iii) constructing an autoregressive model configured to describe a relationship between the estimated plasma insulin concentration at a time t and a difference between two glucose level successive measurements at the times t and t-k, wherein k is equal to the predetermined time interval;
   iv) computing a plurality of parameters of the autoregressive model by using a plurality respective sets of the estimated plasma insulin concentration and the plurality of glucose level measurements at a plurality of times;
   v) calculating an amount of insulin to be delivered at a current time using the autoregressive model and a proportional-integral-derivative (PID) controller respectively, wherein the PID controller calculates the amount of insulin to be delivered based on a difference between the glucose level measurement of the current time and a desirable glucose level and a plurality of predetermined gains;
   vi) tuning the plurality of parameters of the autoregressive model and the plurality of predetermined gains of the PID controller respectively until calculation results of the amount of insulin to be delivered calculated by using the autoregressive model and the amount of insulin to be delivered calculated by using the PID controller are the same, wherein if the calculation results are not the same, the calculation results of the autoregressive model and the PID controller are replaced by average of the calculation results, respectively, to recompute the plurality of parameters of the autoregressive model and the plurality of predetermined gains of the PID controller; and
   vii) determining the amount of insulin to be delivered according to a final calculation result from the tuning step.

6. The artificial pancreas according to claim 5, wherein the controller is one of a processer in the glucose sensor, a processer in the insulin pump, a processer in a handset, or a processing module of a smart device.

* * * * *